United States Patent [19]

Lipton

[11] Patent Number: 4,985,034
[45] Date of Patent: Jan. 15, 1991

[54] SAFETY SURGICAL BLADE, HANDLE AND SHIELD

[75] Inventor: James M. Lipton, Dallas, Tex.

[73] Assignee: Board of Regents, The University of Texas System, Austin, Tex.

[21] Appl. No.: 360,089

[22] Filed: Jun. 1, 1989

[51] Int. Cl.⁵ ............................................. A61B 17/32
[52] U.S. Cl. ...................................... 606/167; 30/162
[58] Field of Search ................. 30/335, 332, 340, 329, 30/284, 285, 162; 606/167, 170, 176, 185

[56] References Cited

U.S. PATENT DOCUMENTS

| | | | |
|---|---|---|---|
| 2,960,769 | 11/1960 | Matwijcow | 30/340 |
| 3,793,726 | 2/1974 | Schrank | 30/151 |
| 3,877,147 | 4/1975 | Cummings | 30/329 |
| 3,905,101 | 9/1975 | Shepherd | 30/162 |
| 3,906,626 | 9/1975 | Riuli | 30/162 |
| 4,617,738 | 10/1986 | Kopacz | 30/339 |
| 4,719,915 | 1/1988 | Porat et al. | 606/167 |
| 4,735,202 | 4/1988 | Williams . | |
| 4,825,545 | 5/1989 | Chase et al. | 30/153 |

Primary Examiner—Mickey Yu
Assistant Examiner—Kerry Owens
Attorney, Agent, or Firm—Arnold, White & Durkee

[57] ABSTRACT

A surgical scalpel is provided consisting of a handle, a blade, and a removable and reattachable blade shield to encase the blade both before and after use and reduce the likelihood of accidental contact with the blade. The blade is retained in the blade shield prior to use through tape or other closure means. Upon removal of the closure means, the forward end of the surgical handle is attached to a handle socket in the base of the blade preferably through a pawl and notch releasable interengagement mechanism, and the blade, securely attached to the handle may be withdrawn from the blade shield. After use, the blade is returned to the blade shield. A force in the direction of the cutting edge of the blade is applied to the handle causing a weakened floor of the handle socket to be displaced and forcing the handle socket walls of the blade base into retaining recesses defined in the blade shield thus securing the used blade within the blade shield. The handle is then withdrawn from the blade base and the handle can be reused. The used blade, secured within the blade shield, may be safely disposed.

9 Claims, 2 Drawing Sheets

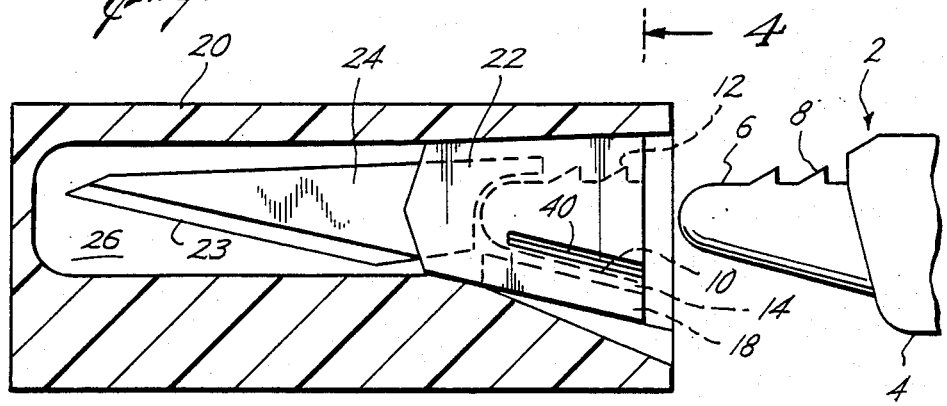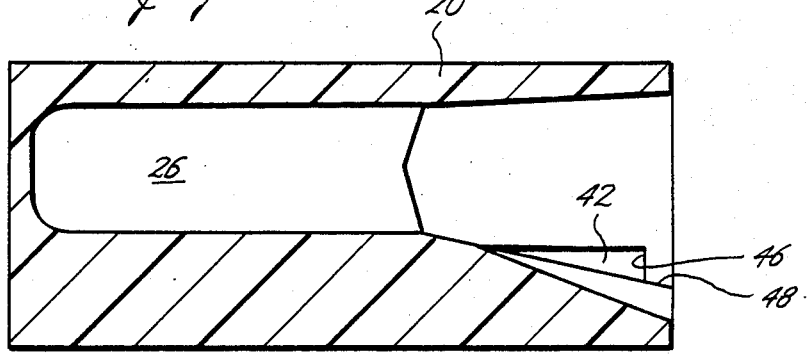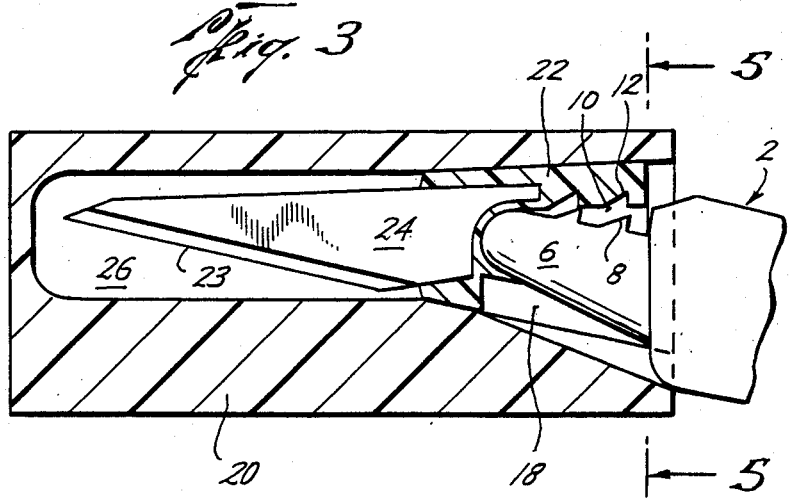

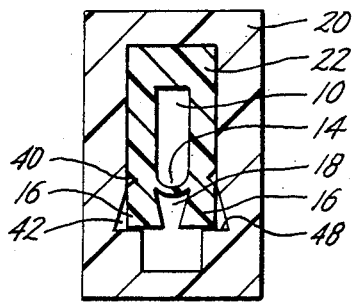
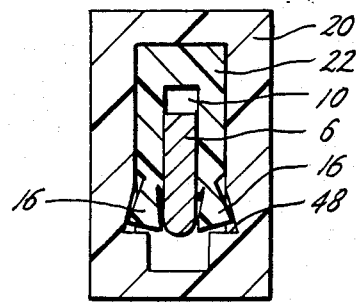
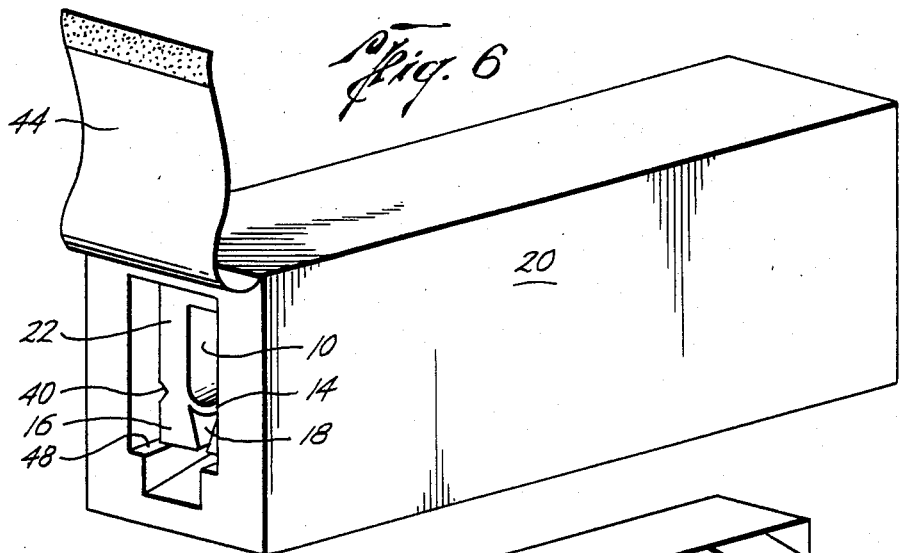
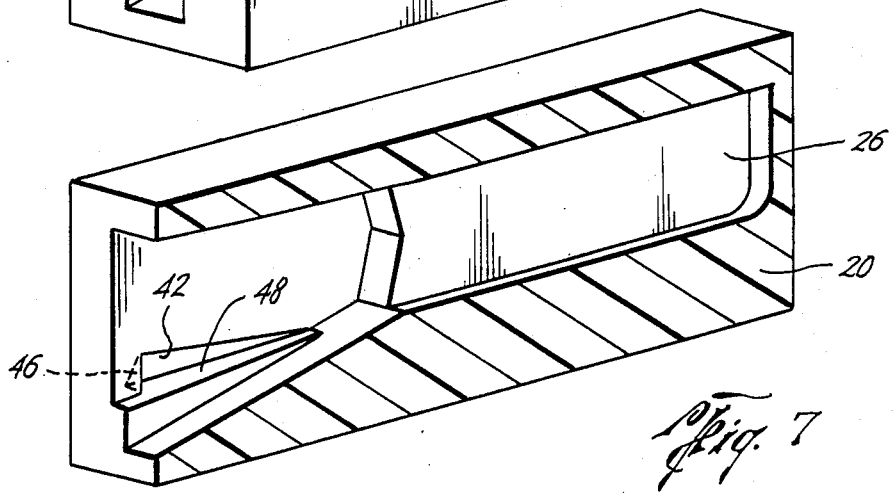

SAFETY SURGICAL BLADE, HANDLE AND SHIELD

BACKGROUND OF THE INVENTION

I. Field of the Invention

The present invention relates generally to a surgical scalpel, and more particularly, to a surgical scalpel with a removable and reattachable blade shield and with a removable and reusable scalpel handle. The invention secures the used blade inside the blade shield by the single step of removing the reusable handle. The blade shield reduces the risk of accidental contact with the used blade.

II. Description of the Related Art

Disposable surgical scalpels and surgical scalpels with disposable blades have long been known. Disposable blades assure the user of a sharp instrument and can serve to reduce the risk of infection. Disposable blades are typically shipped in some type of protective cover such as a cardboard tube or plastic guard. Some blade shields and covers are designed merely to protect the blade in shipment and be discarded after removal from the blade. When blades initially protected by such blade shields are then disposed, the unprotected blades can, unfortunately, cut through plastic disposal bags or accidentally cut the user. Additionally, merely attaching or removing a blade from a handle may require the use of a tool, such as a forceps, and the user risks cuts or damage to the blade.

An unprotected blade, when disposed, may pose a serious risk to those attempting to remove the blade from a reusable handle, those handling a plastic disposal bag containing the blade, and those emptying refuse receptacles in which unprotected blades have been disposed.

Certain types of blade shields may be reused to cover used surgical blades prior to disposal of the blade and handle assemblies. Where a non-removable or non-reusable handle is involved, as in the related art, the user may be less inclined to cover the used blade prior to disposal because the user may simply dispose of the entire blade and handle as a unit. However, problems associated with the disposal of an exposed blade will still exist.

SUMMARY OF THE INVENTION

A surgical scalpel with a handle, removable blade, and removable and reattachable blade shield for encasing the blade is achieved by the present invention. A principal advantage of the present invention is the securing of the used blade in the blade shield when the handle is removed. A reusable handle can encourage the user to remove the blade utilizing the blade shield and avoid accidental reuse of a blade. A reusable handle further allows for a higher quality handle than would be economically feasable where the handle is disposable. The blade shield of the present invention fully encloses the surgical blade protecting it during shipment, when being attached to a handle, when being removed from a handle and, after use, protecting others from accidental cuts or infection from the used blade.

Broadly speaking, the surgical scalpel comprises a handle with a forward end and a rearward grip end to be held by the user, a blade having a forward cutting end and a rearward end where the forward end is a surgical blade and the rearward end is adapted to releasably interengage the forward end of the handle, and a removable and reattachable blade shield for encasing the blade.

The forward end of the handle is adapted to releasably interengage the rearward end of the blade in a releasable locking relation. The forward end of the handle is tapered away from the rearward end of the handle in a preferred embodiment. The locking relation may be established through a pawl and notch system between the forward end of the handle and the rearward end of the blade. The pawl may protrude from the forward end of the handle to mate with a notched handle socket of the rearward end of the blade. Alternatively, a notch may be positioned on the forward end of the handle to mate with a pawled handle socket of the rearward end of the blade.

The rearward end of the blade may include a handle socket and the handle socket preferably contains a weakened section positioned in the direction of the cutting edge of the blade. In a preferred form, the rearward end of the blade further contains a shield breakaway space or chamber abutting this weakened section where the breakaway space or chamber is defined by the weakened section and the walls of the handle socket. The walls of the handle socket define a progressively narrower shield breakaway space when measured in a direction away from the weakened section of the handle socket. The handle socket walls also contain a groove located proximate the weakened section of the handle socket and the grooves are defined on the outer portion of each handle socket wall.

The blade shield comprises a housing with an opening at one end configured for receiving a blade in a longitudinally slidable relation along one orthogonal axis, and a space within the housing able to accommodate different surgical blade sizes and configurations between two opposed longitudinal surfaces of the housing. Preferably, a longitudinal shoulder is provided along each of the two opposed surfaces of the housing, located with each shoulder facing the other longitudinal surface. Additionally, the blade shield may contain recesses defined within the opening able to receive the handle socket walls in a locking relation. Preferably, the recesses are longitudinal and located within each opposed longitudinal surface.

In a preferred embodiment, the scalpel blade has a cutting edge along its forward end and a socket holder along its rearward base end adapted to receive a handle. The blade is configured to slide into the housing through the opening with the blade's forward end projecting into the housing. A first interengaging mechanism retains the used blade in the blade shield through expansible members on the rearward end of the blade which are expanded into laterally opposed recesses within the blade shield. A second releasable interengaging mechanism retains a handle within the socket holder through a notch and pawl mechanism.

In use, the forward end of the handle is inserted in the handle socket of the blade and thus securely attached to the blade so that the blade may be withdrawn from the blade shield. After use, the blade is returned to the blade shield and pressure is applied to the handle in the direction of the cutting edge of the blade. The weakened section of the handle socket is displaced and the downward pressure forces the socket walls, which define a progressively narrower shield breakaway space, to expand into the recesses within the opening in the blade shield. The expanded socket walls thus lock the blade in the blade shield and allow removal of the handle from the handle socket.

The present invention allows the user to remove the handle and secure the blade within the blade shield in a single step.

During shipment, and storage a closure, preferably removable, retains the blade within the blade shield.

BRIEF DESCRIPTION OF THE DRAWINGS

FIG. 1 is a side sectional view of a blade shield of the invention encasing a blade of the invention and a forward end of a handle prior to engagement with the blade base;

FIG. 2 is a side sectional view of a blade shield of the invention;

FIG. 3 shows the shield of FIG. 1 with the handle positioned for removal from the blade base;

FIG. 4 is a sectional view of the shield and blade of the invention taken along the line 4—4 of FIG. 1;

FIG. 5 is a sectional view of the shield and blade of the invention taken along the line 5—5 of FIG. 3.

FIG. 6 is a perspective view of a shield of the invention with a blade positioned within the shield; and, FIG. 7 is a perspective view of a shield of the invention, shown in section.

DETAILED DESCRIPTION OF THE PREFERRED EMBODIMENT

FIGS. 1 and 2 illustrate a preferred embodiment of a surgical scalpel of the invention. As shown in FIGS. 1 and 2, handle 2 includes handle grip 4 at the rearward end and handle forward end 6 at the forward end. The handle forward end 6 preferably tapers to a rounded point away from handle grip 4. Pawls 8 protrude from the handle forward end 6. Immediately prior to use, blade shield 20 houses blade 24 and blade base 22.

The blade shield 20 consists of blade storage area 26 which stores the blade 24 and the blade base 22. The opening in the blade shield 20 leading into the blade storage area 26 and blade storage area 26 are able to receive and contain, respectively, different surgical blade sizes and configurations between the two opposed longitudinal surfaces of the blade shield 20. The blade shield 20 further consists of shield retaining recesses 42, which, in the preferred embodiment are longitudinal recesses within each opposed longitudinal surface of the blade shield 20. The shield retaining recesses 42 can receive expansible handle socket walls 16. Socket retaining recess ridges 46 inhibit the blade base 22 from exiting the blade shield 20 after the handle socket walls 16 are expanded into the shield retaining recesses 42. Blade shield shoulders 48 support the blade base 22 within the blade shield 20. In the preferred embodiment, the blade shield shoulders 48 are longitudinal shoulders along each opposed longitudinal surface of the blade shield 20 facing toward the other opposed longitudinal surface.

The blade base 22 consists of handle socket 10 and notches 12 shown in phantom. The handle socket 10 is shaped to mate with the handle forward end 6, and the notches 12 are designed to mate with the pawls 8 to secure the handle 2 to the blade base 22 in a releasable locking interengagement.

In the preferred embodiment, the blade shield 20 is configured to receive the blade 24 in a longitudinally slidable relation along one orthogonal axis. The cutting edge 23 of the blade 24 is configured to slide from the blade shield 20 for use and slide into the blade shield 20 after use with the cutting end 23 projecting into the blade shield 20.

The blade base 22 is permanently affixed to blade 24 through methods known in the art. In the preferred embodiment, the blade base 22 is made of a strong lightweight thermoplastic that is rigid once formed while retaining sufficient flexibility to allow the socket walls 16 to expand into the shield retaining recesses 42. The blade 24 is preferably made of a surgical steel. As shown in phantom, a portion of the blade 24 is secured within the blade base 22. Thus when the handle 2 is secured to the blade base 22, the user holding the handle grip 4 has firm control of the blade 24.

As shown in FIGS. 1, 4 and 6, the handle socket 10 is defined by the handle socket walls 16 of the blade base 22, that portion of the blade base 22 defining the notches 12, and socket floor 14. The socket floor 14 is a frangible member positioned in the direction of the cutting edge 23 of the blade 24. The socket floor 14 is formed as a frangible or otherwise weakened section of the handle socket 10. The socket floor 14 separates the handle socket 10 from shield breakaway space 18.

The socket floor 14 is made frangible preferably through perforations in the floor 14. Alternatively, the socket floor 14 may be formed of a material more brittle than that of the blade base 22. The socket floor 14 may also be formed of a thickness that allows the socket floor 14 to break under moderate pressure.

One skilled in the art will recognize that the positioning of the pawls 8 and the notches 12 may be reversed. Further, alternate locking mechanisms may be utilized including, but not limited to, a simple friction fit or a raised rib about the perimeter of one surface to interengage a channel about the perimeter of the mating surface. Similarly, the shape of the pawl and notch may be varied from the sloped forward notch of the preferred embodiment, to include but not be limited to, a rounded pawl and notch or a squared pawl and notch. The alternate locking mechanisms and pawl and notch shapes described are merely descriptive of some of the many locking mechanisms and pawl and notch shapes known in the art and are not intended as limitations.

FIG. 3 shows the blade 24 and the base 22 returned to the blade shield 20 being disengaged from the releasable interengagement with the handle forward end 6. Handle forward end 6 is disengaged from the blade base 22 through application of a force applied to the handle 2 in the direction of the cutting edge 23 of the blade 24. This force, shown as downward, causes the socket floor 14 to be displaced and allows the handle forward end 6 to enter the shield breakaway space 18.

As shown in FIGS. 2, 4, 5 and 7, when the blade 24 and the blade base 22 are within the blade shield 20 and force in the direction of the cutting edge 23 of the blade 24 is applied to the handle 2, the handle forward end 6 is forced in a direction shown as downward displacing the socket floor 14 and pressing outward against the handle socket walls 16. The handle socket walls 16 define the shield breakaway space 18 progressively narrower moving in a direction away from the socket floor 14. Therefore, the handle forward end 6 forces the handle socket walls 16, which are expansible, into the laterally opposed shield retaining recesses 42. The socket retaining recess ridges 46 secure the blade base 22 and the blade 24 inside the blade shield 20 thus the blade shield 20 is reattached to and encases the blade 24. The socket expansion grooves 40 allow the handle socket walls 16 to more easily deform into the shield retaining recesses 42 when the handle forward end 6 presses against the handle socket walls 16.

As shown in FIG. 6, tape 44 or other closure means may be used to secure and seal the blade base 22 and the blade 24 in the blade shield 20 prior to use. The tape 44 may also be used to indicate sterility or lack of tampering with the blade base 22 and the blade 24. The tape 44 may be removable.

In the preferred embodiment, the blade shield 20 is made of a thermoplastic although alternative materials, including aluminum, may be utilized. The blade shield 20 need merely be constructed of a material with sufficient rigidity to retain the blade 24 and the blade base 22 and prevent accidental contact with the blade 24.

Further modifications and alternative embodiments of the apparatus of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size and arrangement of parts. For example, equivalent elements or materials may be substituted for those illustrated and described herein, parts may be reversed, and certain features of the invention may be utilized independently of the use of other features, all as would be apparent to one skilled in the art having the benefit of this description of the invention.

What is claimed is:

1. A scalpel comprising:
   a handle having a forward end and a rearward grip end;
   a blade having a forward cutting end and a rearward end adapted to releasably interengage the forward end of said handle, said rearward end comprising a handle socket having a weakened section in the direction of the cutting edge of said surgical blade; and
   a removable and reattachable blade shield for encasing said blade.

2. The device of claim 1 wherein said blade further comprises a shield breakaway space abutting said weakened section and defined by said weakened section and said handle socket walls.

3. The device of claim 2 wherein said handle socket walls define a progressively narrower shield breakaway space in a direction away from said weakened section.

4. The device of claim 2 wherein said handle socket walls each further comprise a groove positioned proximate said weakened section on the outer portion of each respective said handle socket wall.

5. The device of claim 3 wherein said handle socket walls each further comprise a groove positioned proximate said weakened section on the outer portion of each respective said handle socket wall.

6. The device of claim 2 wherein said blade shield comprises an opening for receiving and containing different surgical blade sizes and configurations.

7. The device of claim 6 wherein said blade shield further comprises recesses defined within said opening and able to receive said handle socket walls in a locking relation.

8. A scalpel blade and blade shield comprising:
   a blade shield having a housing defining an opening at one end configured to receive a scalpel blade in longitudinally slidable relation along one orthogonal axis;
   a scalpel blade having a cutting edge along its forward end and a base at its rearward end, said blade configured to slide into said housing through said opening with its forward end projecting into said housing;
   a first interengaging means operable to retain said blade within said blade shield, said means comprising laterally opposed recesses within the blade shield, and expansible members on said base operable to expand into said recesses;
   the base end of said blade defining a socket holder adapted to receive a handle; and
   a second releasable interengaging means operable to retain a handle within said socket holder.

9. The scalpel blade and shield of claim, 8 in which the second interengaging means comprises a notch and pawl mechanism.

* * * * *